(12) United States Patent
Elias et al.

(10) Patent No.: US 7,999,515 B2
(45) Date of Patent: Aug. 16, 2011

(54) BATTERY CHARACTERIZATION TECHNIQUE ACCOUNTING FOR OFFSET ERROR

(75) Inventors: Benjamin N. Elias, Lane Cove (AU); Tony M. Nygard, Lane Cove (AU)

(73) Assignee: Cochlear Limited, Macquarie University, NSW ( * ) Notice: Subject to any disclaimer, the term of this patent is extended or adjusted under 35 U.S.C. 154(b) by 394 days.

(21) Appl. No.: 10/565,210

(22) PCT Filed: Jul. 26, 2004

(86) PCT No.: PCT/US2004/024163
§ 371 (c)(1),
(2), (4) Date: Jan. 20, 2006

(87) PCT Pub. No.: WO2006/022645
PCT Pub. Date: Mar. 2, 2006

(65) Prior Publication Data
US 2008/0054847 A1    Mar. 6, 2008

(30) Foreign Application Priority Data
Jul. 24, 2003   (AU) ................ 2003903839

(51) Int. Cl.
*H02J 7/00* (2006.01)
(52) U.S. Cl. .............................. 320/136; 320/137
(58) Field of Classification Search ............... 320/122, 320/136, 137, 130, DIG. 12, 132, 101; 607/4, 607/5, 9, 27, 29, 137, 32–34, 60, 61; 600/379; 307/66, 46; 381/322–324, 326, 380
See application file for complete search history.

(56) References Cited

U.S. PATENT DOCUMENTS
3,764,748 A * 10/1973 Branch et al. ................... 607/57
(Continued)

FOREIGN PATENT DOCUMENTS
DE          2631974 A1    1/1978
(Continued)

OTHER PUBLICATIONS

International Searching Authority, "International Search Report," issued in connection with International Patent Application No. PCT/US2004/024163, on Feb. 18, 2005 (1 page).
International Searching Authority, "Written Opinion," issued in connection with International Patent Application No. PCT/US2004/024163, on Feb. 18, 2005 (3 pages).
International Preliminary Examining Authority, "International Preliminary Report on Patentability," issued in connection with International Patent Application No. PCT/US2004/024163, on Jul. 5, 2005 (3 pages).

(Continued)

*Primary Examiner* — Adolf Berhane
*Assistant Examiner* — Emily Pham
(74) *Attorney, Agent, or Firm* — Kilpatrick Townsend & Stockton LLP (57) ABSTRACT

The present invention provides a system and method for operating a rechargeable battery, the system comprising: current maintaining device for maintaining a predetermined current to the rechargeable battery until the rechargeable battery reaches a predetermined maximum voltage; voltage maintaining device for maintaining a predetermined voltage to the rechargeable battery until a predetermined minimum current is delivered to the rechargeable battery; determining device for determining a cyclical charge value delivered to the rechargeable battery by the current maintaining device and the voltage maintaining device during a cycle; and a correction device for correcting the determining device when charge is not being delivered to the rechargeable battery, on the basis of the charge value.

32 Claims, 7 Drawing Sheets

U.S. PATENT DOCUMENTS

| | | | |
|---|---|---|---|
| 3,942,535 A | | 3/1976 | Schulman |
| 5,277,694 A | | 1/1994 | Leysieffer et al. |
| 5,279,292 A | | 1/1994 | Baumann et al. |
| 5,411,467 A | | 5/1995 | Hortmann et al. |
| 5,411,537 A | * | 5/1995 | Munshi et al. .................. 607/33 |
| 5,500,561 A | * | 3/1996 | Wilhelm ......................... 307/64 |
| 5,627,472 A | * | 5/1997 | Ofer et al. ..................... 324/435 |
| 5,690,693 A | | 11/1997 | Wang et al. |
| 5,702,431 A | | 12/1997 | Wang et al. |
| 5,758,651 A | | 6/1998 | Nygard et al. |
| 5,814,095 A | | 9/1998 | Muller et al. |
| 5,994,876 A | * | 11/1999 | Canny et al. .................. 320/132 |
| 6,049,210 A | * | 4/2000 | Hwang .......................... 324/428 |
| 6,067,474 A | | 5/2000 | Schulman et al. |
| 6,100,670 A | * | 8/2000 | Levesque ....................... 320/150 |
| 6,227,204 B1 | | 5/2001 | Baumann et al. |
| 6,308,101 B1 | | 10/2001 | Faltys et al. |
| 6,553,263 B1 | * | 4/2003 | Meadows et al. ............... 607/61 |
| 6,570,363 B2 | | 5/2003 | Boberschmidt et al. |
| 6,671,552 B2 | | 12/2003 | Merritt et al. |
| 6,768,286 B2 | * | 7/2004 | Trembley ...................... 320/117 |
| 6,810,289 B1 | | 10/2004 | Shaquer |
| 6,922,591 B2 | * | 7/2005 | Single .............................. 607/57 |
| 7,302,071 B2 | * | 11/2007 | Schumaier .................... 381/326 |

FOREIGN PATENT DOCUMENTS

| | | |
|---|---|---|
| DE | 4414134 | 11/1994 |
| GB | 1575543 A | 9/1980 |
| GB | 2139434 | 11/1984 |
| WO | 2006022645 | 3/2006 |

OTHER PUBLICATIONS

English language translation of "Notification of Reason(s) for Refusal," issued by the Japanese Patent Office in connection with Japanese Patent Application No. 2007-523516, on Sep. 8, 2009 (6 pages).

Halaczek/Radecke, "Batteries and Charging Concepts," 2nd Edition, 1998, p. 148, Franzis' Verlag GMBH.

* cited by examiner

BATTERY CHARACTERIZATION TECHNIQUE ACCOUNTING FOR OFFSET ERROR

CROSS-REFERENCE TO RELATED APPLICATIONS

This application is a national stage application under 35 USC §371 (c) of PCT Application No. PCT/US2004/24163, entitled "Battery Characterization Technique," filed on Jul. 26, 2004, which claims priority from Australian Provisional Patent Application No. 2003903839, filed Jul. 24, 2003. In addition, this application is related to: U.S. Pat. No. 6,227,204, entitled "Device and process for charging of rechargeable batteries of implants," filed May 14, 1999; U.S. patent application Ser. No. 09/654,731, entitled "Transcutaneous Power Optimization Circuit for Cochlear Implant," filed Sep. 5, 2000; U.S. patent application Ser. No. 10/257,170, entitled "Battery Monitor and Power Demand Adjuster," filed Oct. 8, 2002; and U.S. patent application Ser. No. 09/962,898, entitled "Multiple Battery Management System" filed Sep. 25, 2001 and U.S. patent application Ser. No. 10/883,809, entitled "Transcutaneous Power Optimization Circuit for a Medical Implant," filed Jul. 6, 2004. The entire disclosure and contents of the above applications are hereby incorporated by reference herein.

BACKGROUND

1. Field of the Invention

The present invention relates generally to batteries and, more particularly, to managing the charging and discharging of a rechargeable battery.

2. Related Art

When a battery is charged, only one part of the supplied electric power is converted into charge. Another part of this power is converted into heat due to the internal resistance of the battery and, therefore, is lost for recharging. Such power loss can lead to an impermissible temperature rise of the host device. In those applications in which the battery is included in a component which is implanted in a patient, such temperature rise may also damage the surrounding tissue.

A further part of the supplied energy drives secondary electrochemical reactions which, for example, lead to gas evolution within the battery. This more commonly occurs when the battery has reached a higher charging level, for example, when the battery is charged to more than 80% of its nominal capacity. In particular, over years of operation, the capacity ratio of the positive and negative electrodes of a battery cell or cells shifts due to electrolyte loss and passivation and/or corrosion of the electrode surfaces. As a result, during charging (i.e., re-charging), a greater and greater preponderance of the gas-forming over the gas-consuming reactions occurs, and thus, the internal pressure of the cell rises quickly during charging. As the gas pressure rises, the cell housing swells, which under certain circumstances can lead to destruction of the cell or the device in which the cell is housed. The increasing corrosion and/or passivation of the electrodes and the concomitant decrease of the electrolyte-wetted electrode surface cause an increase of the internal resistance of the battery.

Thus, a charge management scheme is quite important in rechargeable batteries particularly if the batteries are to be used in an implantable device. Charge management regimes for rechargeable batteries are designed to maximize the useful life of the rechargeable battery by aligning their operating parameters with those empirically shown to be favorable for longevity. Furthermore, such charge management regimes seek to maximize the efficiency of the battery while addressing the adverse consequences associated with charging a battery.

The success of a charge management regime can depend on the accuracy of the input parameters used, such as the amount of charge remaining in the battery at any particular moment in time. One method of determining the charge remaining is to take measurements of the terminal voltage and use this to calculate accumulated charge.

However, voltage correlation techniques can be inaccurate due to variations in a battery's charging and discharging characteristics over its lifetime. These variations can be influenced by the manner in which the battery has been previously charged and discharged, and from the operating temperature. Clearly, this inaccuracy can lead to the undesirable consequences including those discussed above.

Another method of determining the charge remaining is to periodically sample the current flowing into or out of the battery. This method may generate a more accurate estimate of the present state of charge, and measurement gain or offset errors could be corrected using software signal processing techniques. To reduce quantization errors when sampling, the current resolution must be small relative to both charge and discharge currents. The main drawback to this method is its high processing requirement. This is particularly the case where the charge or discharge current is not constant over time. Such sampling needs to be at a rate of at least twice the highest component frequency (the Nyquist rate) of the current waveform, which may require a significant amount of processing power. In many electronic devices, this increased processing burden is impractical because of the limited space and power constraints.

Another method of determining the charge remaining is to mathematically integrate the measured charge and discharge current. The current integration approach has been used for example in U.S. Pat. No. 4,678,999 ("Schneider"). Similarly, U.S. Pat. No. 6,049,210 ("Hwang") has highlighted the usefulness of frequency measurements derived from an integrator. U.S. Pat. No. 6,504,344 ("Adams") demonstrates the integration technique used over a short period of time and under a known load to characterize the battery. However, a drawback of the current integration approach is that inaccuracies can result from the inherent offsets in analog circuitry. Compensation for these offsets has been shown to be more difficult to achieve for lower currents.

It is desired to ameliorate any one or more of the foregoing drawbacks of the above conventional techniques.

SUMMARY

In accordance with one aspect of the invention, there is provided a method of managing a power supply for an electronic device, the power supply having a rechargeable battery source and an auxiliary power source, said method comprising the steps of: implementing a measuring circuit to measure parametric data of the rechargeable battery source during operational charging and discharging cycles with the electronic device; checking for temporary removal of the rechargeable battery source from operation of the device; and testing the measuring circuit for offset error, if power from the rechargeable battery source has been temporarily removed, before resuming said implementing step.

In accordance with another aspect of the invention, there is provided a system for a power supply for an electronic device, said power supply comprising: a rechargeable battery source configured for cyclical charging and discharging by said electronic device; a measuring circuit for measuring parametric data during said charging and discharging; an auxiliary power source being able to power said electronic device independently of said battery source; and a testing circuit for testing said measuring circuit for offset error; and a circuit for reducing current flow from said rechargeable battery to said device to a minimal value; wherein said testing circuit is enabled during said isolation of said rechargeable battery from said device.

In accordance with another aspect of the invention, there is provided a system for operating a rechargeable battery, said system comprising: current maintaining means for maintaining a predetermined current to said rechargeable battery until said rechargeable battery reaches a predetermined maximum voltage; voltage maintaining means for maintaining a predetermined voltage to said rechargeable battery until a predetermined minimum current is delivered to said rechargeable battery; determining means for determining a cyclical charge value delivered to said rechargeable battery by said current maintaining means and said voltage maintaining means during a cycle; and correction means for correcting said determining means when charge is not being delivered to said rechargeable battery, on the basis of said charge value.

In accordance with another aspect of the invention, there is provided an apparatus for characterizing a rechargeable battery, said apparatus comprising: a current limited source for delivering, during a first charging stage, a current flow to said rechargeable battery, until said rechargeable battery reaches a predetermined maximum voltage; a voltage limited source for maintaining, during a second charging stage, a substantially constant voltage to said rechargeable battery, until a current flow delivered to said rechargeable battery is below a predetermined minimum current; an integrator configured to integrate current flow delivered to said rechargeable battery during the first and second calibration stages; threshold detector means configured to signal a unit count of charge upon detection of a predetermined level of charge indicated by the output from said integrator; and correlator configured to correlate a total number of unit counts of charge during said first and second calibration stages with said predetermined maximum voltage and said predetermined minimum current.

In accordance with another aspect of the invention, there is provided computer readable medium, having a program recorded thereon, where the program is configured to make a computer execute a procedure to operate a rechargeable battery, said procedure comprising the steps of: characterizing the battery comprising the sub-steps of: delivering a substantially constant current to said rechargeable battery until said rechargeable battery reaches a predetermined maximum voltage; delivering a substantially constant voltage to said rechargeable battery until a predetermined minimum current is delivered to said rechargeable battery; and determining a delivered charge value delivered to said rechargeable battery by the sub-steps; and cyclically charging and discharging of said rechargeable battery according to said determined delivered charge value.

In accordance with another aspect of the invention, there is provided a battery charger for an electronic device, said battery charger comprising: a rechargeable battery source configured for cyclical charging and discharging by said electronic device; a measuring circuit for measuring parametric data during said charging and discharging; an auxiliary power source being able to power said electronic device independently of said battery source; and a testing circuit for testing said measuring circuit for offset error; and a disconnection circuit for isolating current flow from said rechargeable battery to said device; wherein said testing circuit is enabled during said isolation of said rechargeable battery from said device.

In accordance with another aspect of the invention, there is provided a prosthetic hearing implant system comprising: a battery charger comprising: a rechargeable battery source configured for cyclical charging and discharging by said electronic device; a measuring circuit for measuring parametric data during said charging and discharging; an auxiliary power source being able to power said electronic device independently of said battery source; and a testing circuit for testing said measuring circuit for offset error; and a disconnection circuit for isolating current flow from said rechargeable battery to said device; wherein said testing circuit is enabled during said isolation of said rechargeable battery from said device.

BRIEF DESCRIPTION OF THE DRAWINGS

The invention will be described in conjunction with the accompanying drawings, in which.

DETAILED DESCRIPTION

A starting point in developing a charge management regime for a rechargeable battery is to determine a method to measurably characterize the battery. This normally involves determining the remaining charge capacity in the battery, which can be ascertained in a number of ways. As earlier mentioned, the voltage of the battery can be used, in which case a measurement is regularly taken and an algorithm is implemented that attempts to estimate the amount of useful energy stored in the battery, and therefore may approximate the time remaining until the battery must be recharged.

However, such voltage-based calculations do not take into account the fact that the voltage depends on the chemistry, the current state the chemistry is in, i.e., ageing, the state of charge, and both, the load and the duration of load connection. Fading results in a reduced capacity, i.e., less charge can be stored in and retrieved from the battery. Ideally, a charge management algorithm using this voltage data would be fading-independent, but since only voltage data is known, the algorithm can only approximately compensate for fading effects.

Figure 1:
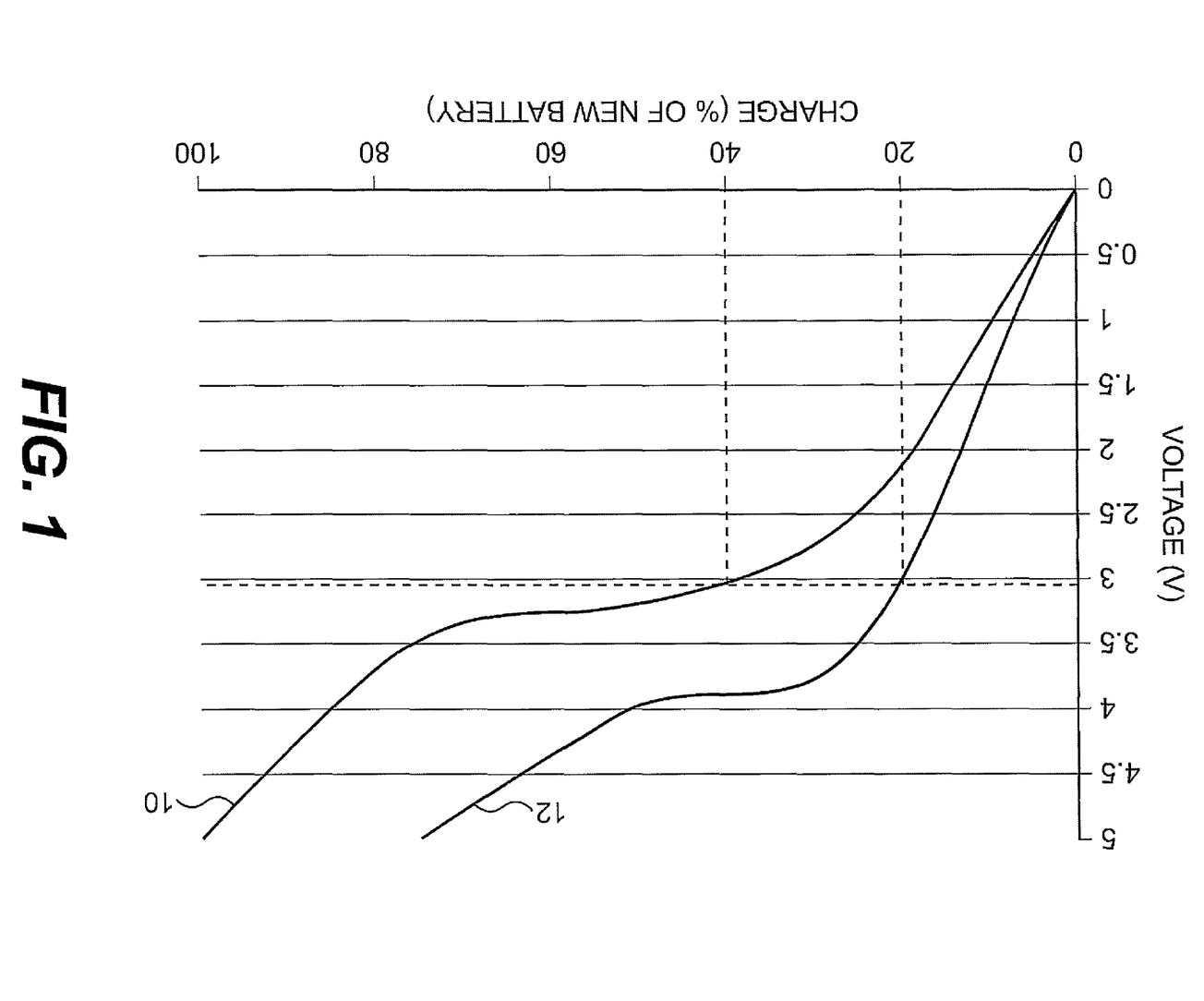
FIG. 1 is a graphical representation of exemplary rechargeable battery fading characteristics.

These variations due to fading can be shown on a plot of charge versus voltage, as shown, for example, in FIG. 1. For a new battery, illustrated by curve 10, there is very little charge remaining below 3.6V, while an aged battery, illustrated by curve 12, has an almost linear relationship between charge and voltage. When new, a charge of approximately 40% of the battery capacity would be required to charge the battery from 0 to 3V. When aged, the battery would require approximately 20% of its capacity to achieve the same result. Consequently, voltage measurements do not represent a linear or otherwise easy-to-define relationship with the actual state of charge of a battery.

In contrast with the above and other conventional techniques, embodiments of the present invention are directed to a re-settable measuring circuit 30 and relating methodologies. Re-settable measuring circuit 30 will first be described with reference to FIGS. 2 and 3, respectively. Thereafter, with reference to FIG. 4, one embodiment of the re-settable measuring circuit 30 and method will be described in the context of one application, a charge management system for charging and discharging a battery.

Figure 2:
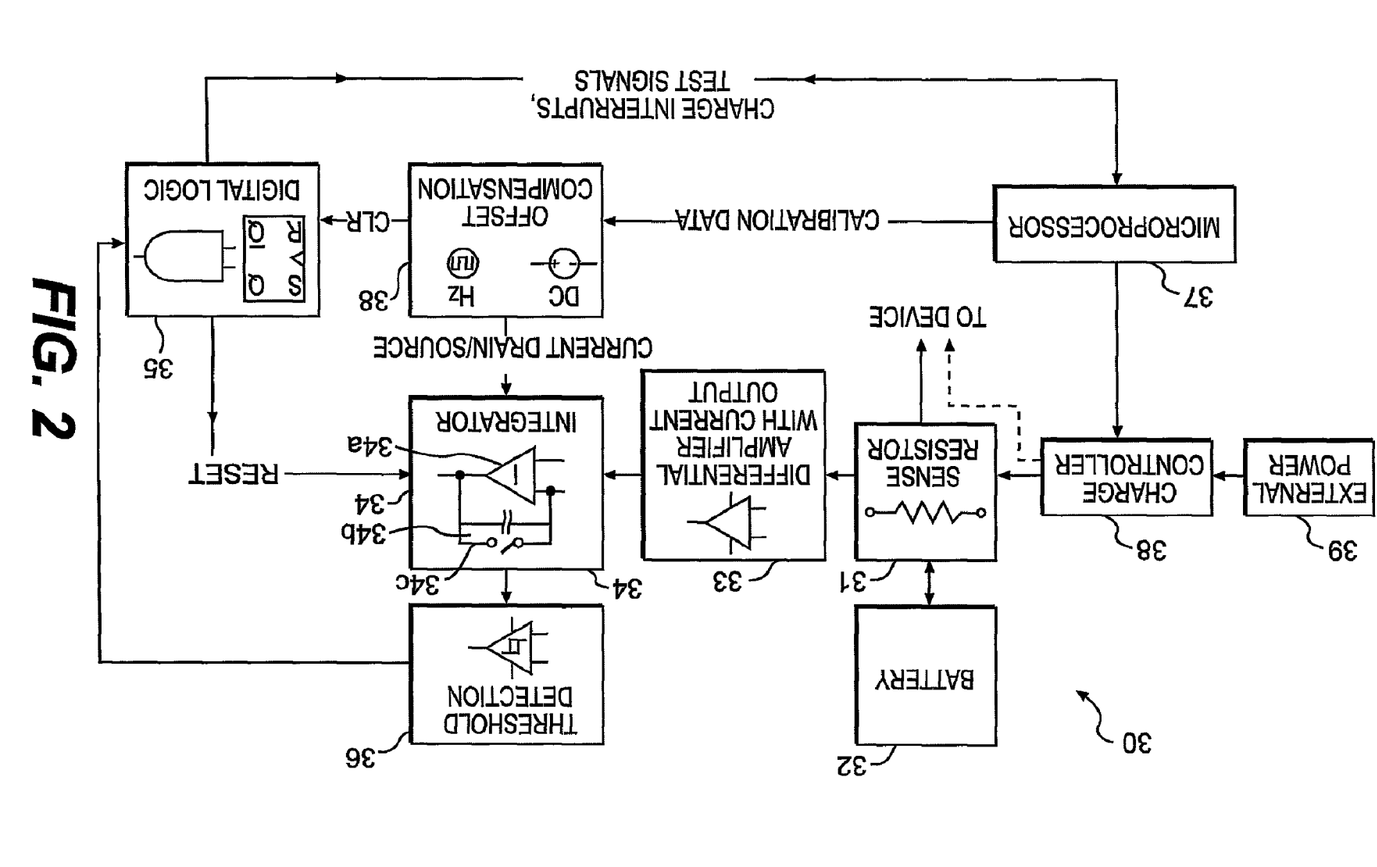
FIG. 2 is a functional block diagram of a re-settable measurement circuit according to one embodiment of the present invention.

Referring to FIG. 2, a sense resistor 31 converts the current flowing into or out of a battery 32 into a voltage drop suitable for amplification. The value of sense resistor 31 is small so that the power of battery 32 is not wasted on current measurement, as this resistance will dissipate some power. Typically, the sense resistor will be in the range of 10 milli ohms to 1 ohm. In one embodiment, as will be discussed below, the sense resistor 31 is 1 ohm.

A differential amplifier 33 is connected across sense resistor 31 and isolates the measurement circuitry from the main power circuit carrying current flow to or from battery 32. Differential amplifier 33 amplifies the voltage drop across sense resistor 31 to a level sufficient to reduce noise and provide a stable signal. In one preferred embodiment, this gain would be on the order of 20 although other values can be used as well. Differential amplifier 33 outputs a current signal, $I_{Diff}$, that is proportional to the current flow in or out of the battery 32, $I_{Batt}$, such that:

$$I_{Diff} = kI_{Batt}$$

where k is a constant. In one embodiment, k=1/22500.

The output current signal, $I_{Diff}$, from differential amplifier 33 is provided to integrator 34. Integrator 34 primarily includes an operational amplifier 34a with a capacitor 34b connected between the output and the inverting input of operational amplifier 34a. In a one embodiment, capacitor 34b, has a capacitance, C, of 100 pF +/−20%, although other values can be implemented. As illustrated in FIG. 2, switch 34c is arranged in parallel to capacitor 34b. Neglecting the effects of non-ideal circuitry, integrator 34 produces an output voltage, $V_{out}$, in accordance with the function:

$$V_{out} = -\int \frac{I_{Diff}}{C} dt$$

or $$V_{out} = -k \int \frac{I_{Batt}}{C} dt$$

When the output voltage from integrator 34 reaches a threshold value, detection block 36 outputs a signal to digital logic 35, indicating that a quantized unit of charge has been processed. Digital logic 35 then resets integrator 34 by temporarily closing switch 34c which, in turn, discharges capacitor 34b. In one embodiment, the integration time is proportional to the input current, the integration capacitor and the threshold voltage. Preferably, the reset time is as short as possible, so as to more closely approximate continuous integration. Hence, the integration time is much greater than the reset time. In one embodiment, the reset time is 3 μs and the maximum charge current is 15 mA. The reset threshold was chosen to 2V. This gives an integration time of 300 μs, although it will be realized that the effective reset time should be as short as possible. There is also an upper limit of the threshold limited by the output range of the integrator and the input range of the comparator.

When the output voltage from integrator 34 again reaches the threshold value, the detection block 36 outputs an additional a further signal to digital logic 35, indicating that another quantized unit of charge has been processed.

Digital logic 35 maintains a directional count of the number of threshold detections received until a predetermined number of threshold detections is reached. In one embodiment, the predetermined number of threshold detections determines the resolution of unit charge. In one embodiment, the resolution is 0.64 μAh (or 2.3 mC). This is achieved with a count value of 128. This predetermined number of threshold detections is also referred to as the logic count value.

Thereafter, digital logic 35 generates an asynchronous interrupt for processing by microprocessor 37. Microprocessor 37 may be any commercially available microprocessor now or later developed. Alternatively, the microprocessor may be a custom developed microprocessor of microcontroller. The asynchronous interrupt signal includes information about the direction of charge flow.

During the calibration routine, no load is placed on battery 32. This generates an open circuit that will prevent current or charge flow from flowing from battery 32 to the load or device. Alternatively, the battery load current may be reduced to a very low value, e.g. by a low power state of the device. During the calibration routine, microprocessor 37 can read data from digital logic 35, including the direction of charge flow to battery 32. Microprocessor 37 can also write data to digital logic 35. An example would be to increase the logic count value, to thereby increase the precision of the offset calculation, given a constant timer resolution. Optionally, the internal, directional count of threshold detections in digital logic 35 could be visible to microprocessor 37. Preferably, the microprocessor 37 is supplied from a power source other than the battery during the calibration routine.

Having commenced the calibration routine, microprocessor 37 calculates an effective offset current value for integrator 34. It is noted again that this calculation is based on the measurements taken from differential amplifier 33 and integrator 34 when no load is placed on battery 32. Once the effective offset has been calculated, microprocessor 37 sets appropriate compensation values. Criteria utilized to determine these compensation values are discussed below. In another implementation, microprocessor 37 determines the effective offset with compensation already applied, and then changes the compensation parameters accordingly. The following three methods are examples of how the offset compensation for the integrator 34 can be implemented, once the effective offset current value is calculated. These are examples only; other methods can be used as will be apparent to those of ordinary skill in the art.

1. Variable bias current: a variable bias current source or sink is provided at integrator 34 input. The bias current has the same magnitude, but with opposite sign, as the equivalent offset current flowing into or out of integrator 34. As referred to above, the bias current is set by the microprocessor 37 under the condition of zero charge current, a known state.

2. Software calibration: The effective offset current is measured and an amount of charge, proportional to the offset current, is periodically added or subtracted to the software count of the charge. This is equivalent in magnitude to the periodic interrupt that microprocessor 37 would receive due solely to the offset error, but opposite in sign. However, this calibration method means that the integration becomes time-dependent, which is undesirable in an asynchronous interrupt-driven system. Also, an increased number of microprocessor instructions are used to store and manipulate time as well as charge data.

3. Variable reset clock: This is similar to the software calibration technique, but implemented in hardware. The frequency of the interrupts generated by the digital logic 35 is measured by microprocessor 37 under the condition of zero charge flow. A clocking signal is generated which has the same frequency as the threshold resets due solely to the offsets. This is then used as an input to digital logic 35, and increments or decrements the internal state of digital logic 35, similar to a threshold reset being generated, but without resetting integrator 34. In this arrangement the errors due to differential amplifier 33 and integrator 34 are still present, but are corrected before interrupts are generated for microprocessor 37. This frees microprocessor 37 from any additional offset calculation once the clocking frequency is set. The clock generation could be, but is not limited to being, implemented using a relatively fast system clock signal and a programmable clock divider to generate a programmable frequency.

Since offset effects of differential amplifier 33 and integrator 34 are compensated for, the measurement is useful even if a small current load is presented to battery 32. In this embodiment, it is not essential for there to be a no load, so long as the value known although it is noted that the more precisely this value is known, the better.

Re-settable measurement circuit 30 preferably relies on the device being temporarily powered from an external power supply 39 other than battery 32. This temporary calibration time can be around 30 seconds for example.

The main advantage of performing calibration in this way is that it may be performed at any time when external power supply 39 is available, typically when charging via charge controller 38. Therefore, the offset compensation maintains its accuracy over the entire range of current when charging or discharging and ensures that errors do not accumulate over time. Also, since the offset compensation is calculated during zero load periods, no pre-testing is required.

Re-settable measurement circuit 30 can be incorporated into a charge management system, as described below. It is noted that at this stage in such an algorithm, the external conditions such as sufficient external power and zero charge current, are assumed to be appropriate for the duration of calibration.

The techniques according to this embodiment of the invention can compensate for battery self-discharge and thus can be applied to a relatively wide range of battery technologies. Self-discharge is more significant in older technologies.

Li-Ion technology, for example, is very sensitive to certain parameters. For instance over-charge and over-discharge may result in permanent damage and reduced performance for all rechargeable chemistries. The performance of the battery is also dependent on the level of charge stored on the battery when operating within the operating limits.

Further, the processing burden is minimized, given that a combination of analog and digital techniques are used. It is also noted that this benefit is further realized through the use of interrupts to the microprocessor, rather than processor polling. So instead of a processor periodically recording how much charge has accumulated, an interrupt is generated, which tells the processor that a quantized unit of charge has been received. This event may occur relatively infrequently, requiring minimal processor time to store this information.

The techniques according to certain embodiments of the present invention can be advantageously used with devices powered by batteries with a processor used in part for battery charge management. Some embodiments of the present invention are particularly applicable to situations where a system must determine the charging regime for the battery. That is, to preserve battery life, the battery may not necessarily be charged even if it is possible to do so.

The techniques according to certain embodiments of the present invention make some attempt at minimizing errors at the design level, but accept them as being finite and non-zero. Under a no-load condition, these errors are quantified. Then, during measurement, an error compensation technique minimizes the error. That is, it can be calibrated during operation.

Figure 3:
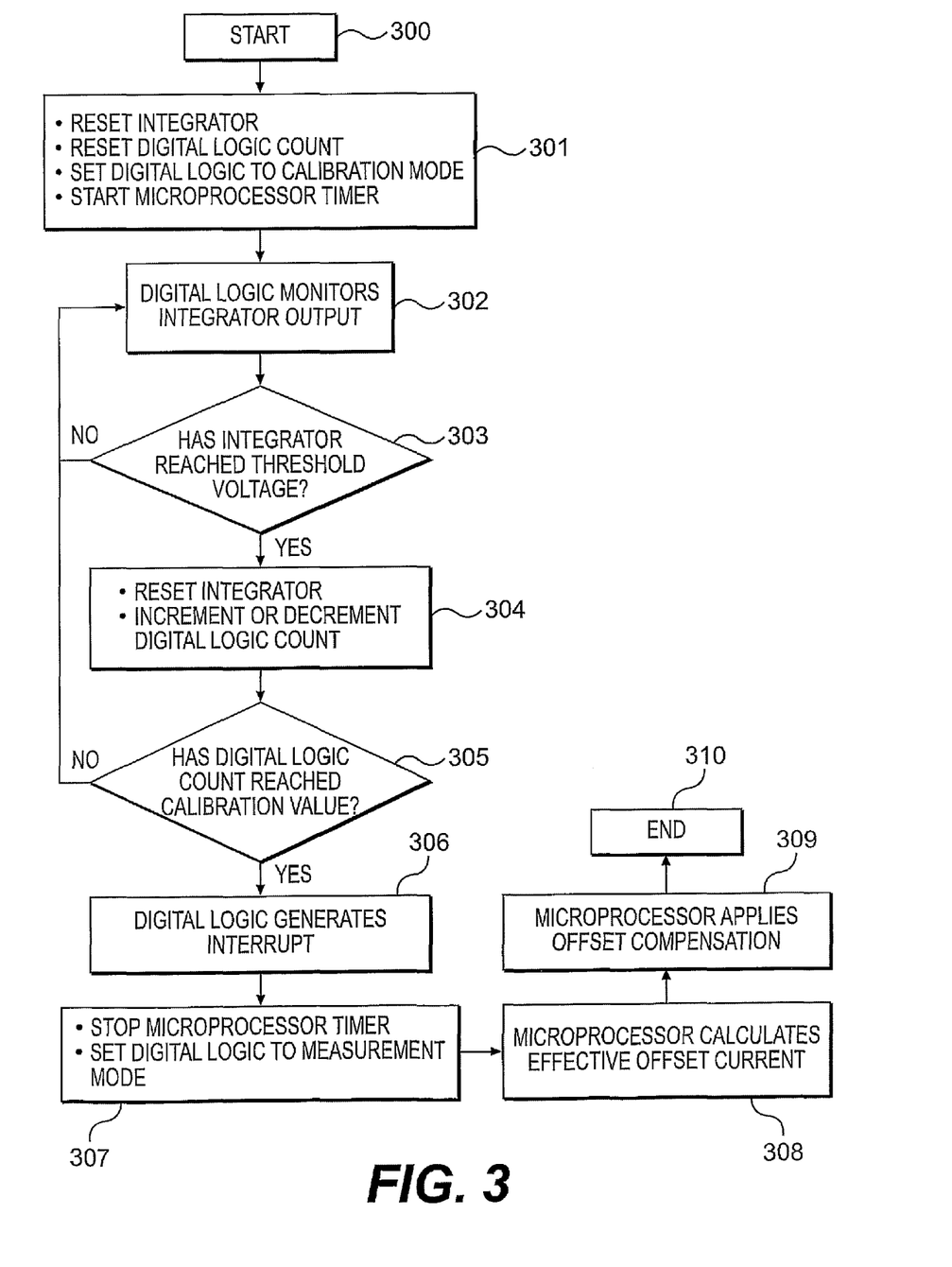
FIG. 3 is a flow chart of one embodiment of the calibration of the measurement circuit illustrated in FIG. 2.

FIG. 3 is a flow chart of one embodiment of how embodiments of re-settable measurement circuit 30 can be used in accordance with the teachings of the present invention. Proceeding to step 301, integrator 34 is initialized, the digital logic internal count is reset, and digital logic 35 is placed in calibration mode before advancing to step 302 in which the output of integrator 34 is monitored. During step 301, microprocessor 37 starts a timer, for use later when determining effective current.

The voltage output of integrator 34 is continuously checked for comparison with a threshold voltage at step 303. Once the threshold voltage value has been reached, step 304 is taken to reset integrator 34 and to increment digital logic circuit 35 internal count.

Next, at step 305, digital logic circuit 35 internal count is checked for having reached a calibration count limit value and until this is reached, the output of integrator 34 is continued to be monitored by reverting back to step 302. However, once the digital logic circuit 35 internal count has reached the calibration count value, the digital logic circuit 35 generates an interrupt for microprocessor 37 at step 306.

Microprocessor 37 processes this interrupt at step 307, by recording a timer value and placing digital logic circuit 35 back in measurement mode, for future current measurements.

At step 308, microprocessor 37 calculates the effective offset current on the basis of the recorded timer value and the amount of current represented by the calibration count value. Current is charge per unit time. Although this charge has been measured, it did not actually flow into or out of the battery.

At step 309, microprocessor 37 takes steps to compensate for the measurement offset as earlier described, and the calibration routine ends at step 310.

Figure 4:
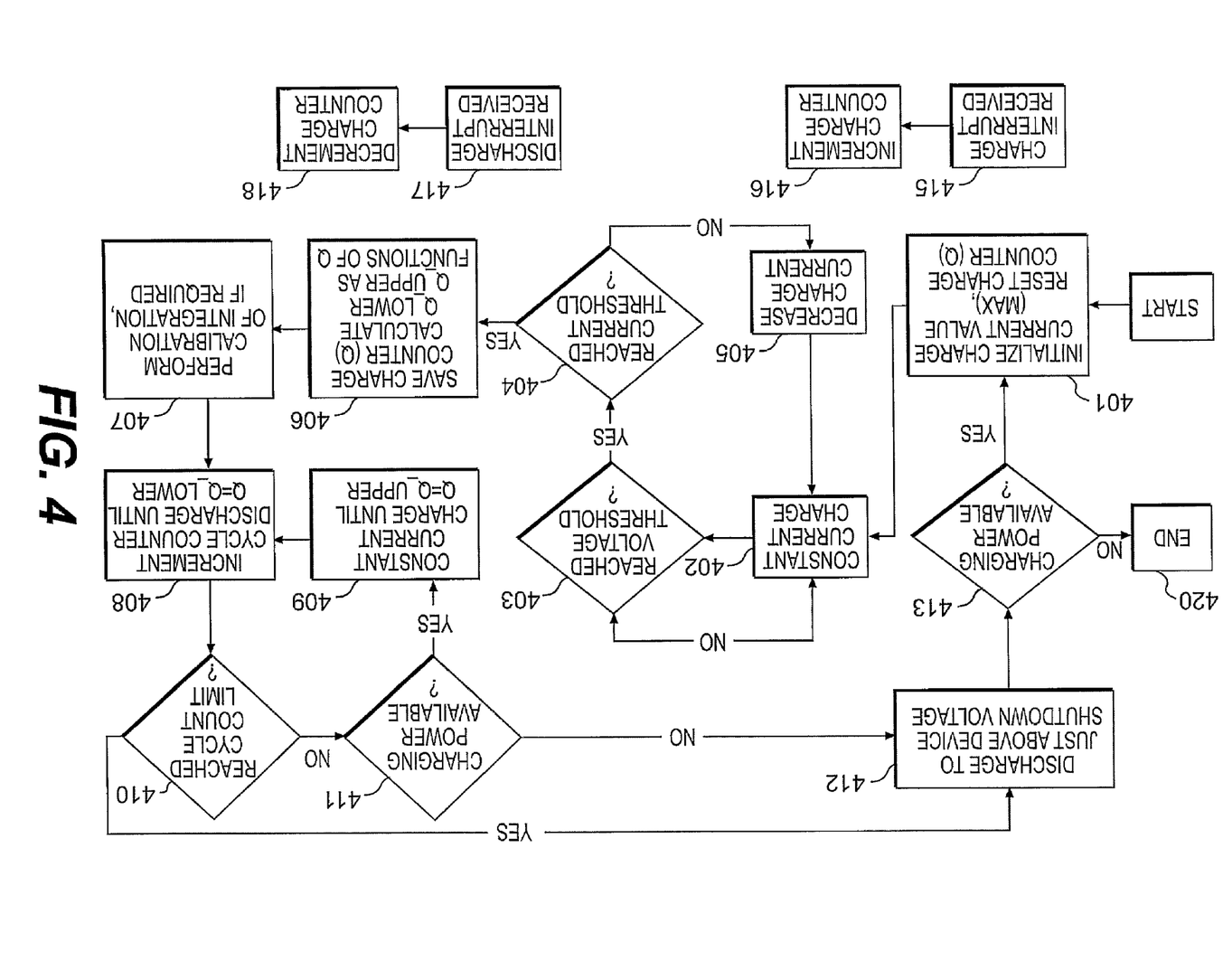
FIG. 4 is a flow chart of one embodiment of a charge management algorithm for charging and discharging a battery.

Referring now to FIG. 4, an example of a charge management scheme, for charging and discharging battery 32, incorporating the re-settable measurement circuit 30 of FIGS. 2 and 3 will be described. It is noted that this is provided as an example, and the methods outlined above are not limited to this particular scheme, which is based on the current/voltage limited method. Other schemes could be based on power limited and fast charge methods, including pulse charging.

In summary, the charge management scheme first discharges battery 32 to a known state, then uses the method of limited current, then limited voltage to initially charge the battery. During this time, the amount of charge delivered to battery 32 is recorded. The battery is then cycled using the amount of charge stored as a measure of the useful energy left in the battery. This process is repeated after a number of cycles to eliminate any accumulated error due to imprecise charge integration.

The method commences by initializing the following variables:

VOLTAGE THRESHOLD—set at say preferably in one embodiment between 2.0 and 6.0 Volts and in an alternate embodiment of between 1.0 and 50 Volts. The voltage threshold is reached by applying a constant charging current in a preferred embodiment. It should be appreciated that this threshold may be achieved by any means know in the charging art.

CHARGE CURRENT—set with a maximum allowable constant charging current value. Typically, the current limit is programmable in steps, for example in 0.5 mA steps, from zero to the maximum allowable limited current value.

CURRENT THRESHOLD—set at a proportion of the capacity of battery 32, say between capacity/10 and capacity/100. The value stored in this variable represents a lower limit of CHARGE CURRENT, and is used to determine the end point of the limited voltage process.

CHARGE COUNTER (Q)—a directional count of the number of charge interrupts generated by digital logic 35, which thus represents a cumulative value of charge. This variable is initially set to zero.

Q_LOWER—represents a lower value of charge reached during the operation cycle.

Q_UPPER—represents an upper value of charge reached during the operation cycle.

CYCLE COUNTER—holds value of cycles and is initially set at zero.

CYCLE COUNT LIMIT—set to between 20 and 100 cycles.

OFFSET COMPENSATION—set to zero, unless there is an existing valid value, in which case that value is retained.

After initialization, step 402 is proceeded to, in which a constant charging current is applied to battery 32 in accordance with the value stored in CHARGE CURRENT.

Throughout the method, except during calibration at step 407, the value stored in CHARGE COUNTER (Q), reflects the cumulative amount of charge delivered to battery 32, and is incremented or decremented accordingly.

Once the battery voltage reaches the value stored in VOLTAGE THRESHOLD, the limited voltage charge phase is commenced. This is indicated by decision diamond 403. Here the voltage is maintained but the current is decreased until it reaches the value held in CURRENT THRESHOLD as indicate by decision diamond 404.

As a safety feature, the maximum voltage of battery 32 during charging is limited by hardware and can therefore never be exceeded. When VOLTAGE THRESHOLD is set to a lower value than the hardware limit, the charge current can be limited by microprocessor 37. Another safety feature of the present method is that if CHARGE COUNTER (Q) falls below zero during discharge, the device may treat this as an error condition and reset itself accordingly.

Figure 5A:
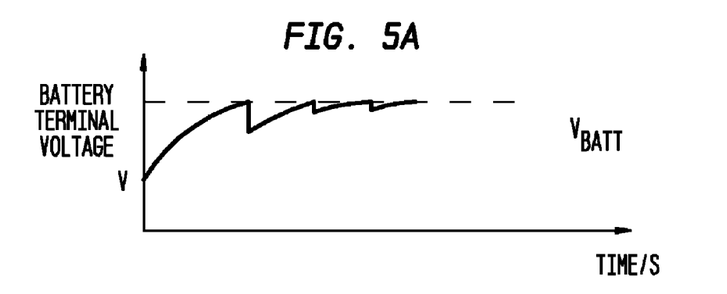
FIGS. 5A and 5B are each a graphical representation of charging characteristics of an initial charging cycle for one embodiment of the charge management algorithm of FIG. 4.
Figure 5B:
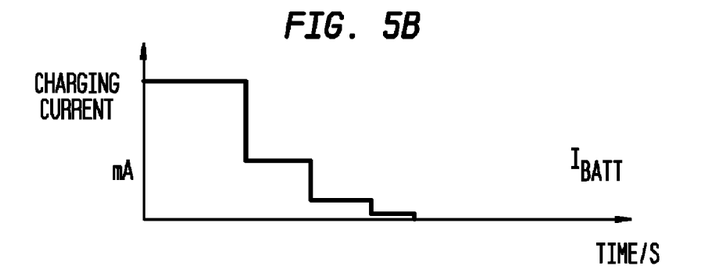

An example of the result of the present method is shown in FIGS. 5A & 5B, in which it can be seen that the limited current charge is applied to the battery until the terminal voltage reaches a threshold voltage. Thereafter, the current is repetitively decreased and the battery is charged until the terminal voltage again reaches the threshold voltage. This allows the internal chemistry of battery 32 to settle to a steady state. Hence, battery 32 can subsequently be discharged under well-defined conditions from an unknown state of charge to a well-defined cut-off voltage.

The discharging could be iteratively reduced by a fraction in one arrangement. However, the charge current should usually not fall below a limiting value specified by the manufacturer, in order to avoid accelerated battery fading.

The limited voltage phase is protected against indefinite charging, which could result in permanent loss in performance. As battery 32 fades, the limited current phase becomes shorter and the limited voltage phase becomes longer. Battery 32 starts to accept the charge at a slower rate.

Once the current decreases to the value held in CURRENT THRESHOLD, a single charging cycle is completed and thus allows integrator 34 offset calibration to be implemented. This occurs when the method proceeds to step 406.

At step 406, the value stored in CHARGE COUNTER (Q), which now reflects a cumulative quantity of charge stored in battery 32, is used to calculate values that are written to Q_LOWER and Q_UPPER. These calculated values will vary over time as battery 32 fades, since the accumulated charge stored in CHARGE COUNTER (Q) will decrease, for the same voltage and current thresholds.

The value stored in CHARGE COUNTER (Q), for the first execution of the method loop, could be incorrect due to calibration not having been performed. Since the calibration will be performed before the second execution, this effect will only be applicable for a short period of device operation.

Next, at step 407, the integration function can be calibrated by correcting any offset error, as explained previously, if sufficient external power is available for the device to function. This is a requirement, as no load must be placed on the battery during calibration. At this stage the offset compensation parameters are written to OFFSET COMPENSATION.

After the calibration of step 407 is completed, step 408 is proceeded to. At step 408, battery 32 is allowed to discharge until the value stored in CHARGE COUNTER (Q) is equal to the value stored in Q_LOWER. Thereafter, the CYCLE COUNTER is incremented.

At step 409, battery 32 is again charged until the value of CHARGE COUNTER (Q) is equal to the value stored in Q_UPPER. Thereafter the process is handed over to step 408 and the cycle repeats. This cycle results in an oscillation between a minimum and maximum charge counter value.

Figure 6A:
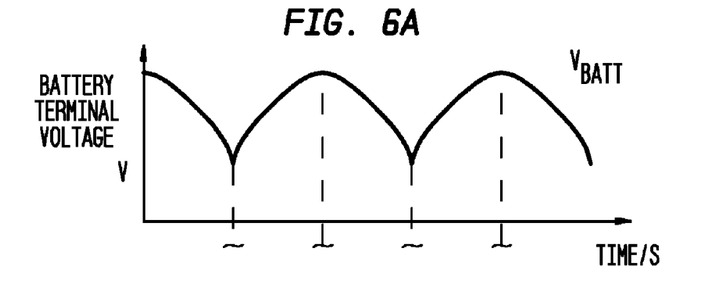
FIGS. 6A and 6B are each a graphical representation of charging characteristics of a subsequent charging cycle for one embodiment of the charge management algorithm of FIG. 4.
Figure 6B:
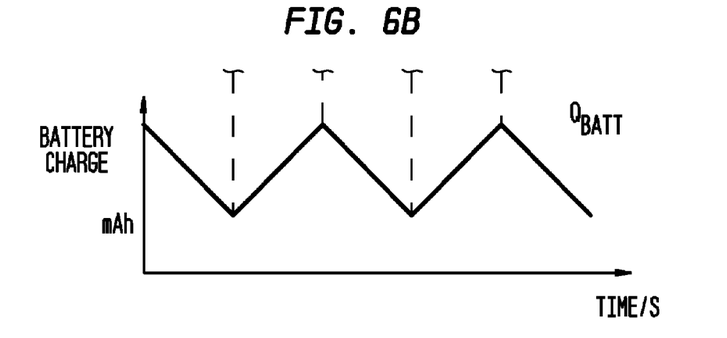

An example of the cycling performed by steps 408, 409, 410 and 411 is shown in the graph of FIGS. 6A & 6B. These subsequent discharge and charge actions may be partial ad illustrated or full, depending on the desired result.

Step 412 is preceded to when CYCLE COUNTER is equal to CYCLE COUNT LIMIT, as determined by step 410. The process of recalibrating the measuring circuit occurs at around every 20 to 100 operating (charge/discharge) cycles of the present method. It should be appreciated that this range may be adjusted up or down based on the amount of processing power available and on the accuracy desired. In this context, it is noted that any charge followed by a discharge event is referred to as a cycle and does not imply full charge or full discharge of battery 32.

In the case of charging power or external power supply 39 becoming unavailable as determined in step 411, the method proceeds to step 412. At step 412, battery 32 is discharged to a well-defined cut-off voltage. Thus, it should be appreciated that the cut-off voltage may vary considerably between different applications. This limitation protects battery 32 against damage from over discharging. This cut-off voltage is typically specified by the battery manufacturer, and is dependent on the battery technology used. Thus, it should be appreciated that the cut-off voltage may vary considerably between different applications.

At step 413, the presence of charging power from external power supply 39 is determined. If there is no charging power available, then the method ends by proceeding to step 420. Otherwise the method proceeds to step 401 and the method repeats.

The method described above, which incorporates re-settable measurement circuit 30, is relatively aging-independent and can therefore provide the following advantages:

1. Improved battery cycle life: This occurs because the techniques described herein can allow battery 32 to be operated within its designed limits, but closer to maximum performance. Also, the time for battery 32 to discharge before an external power supply 39 is required to power the electronic device can be made longer without adversely affecting battery longevity. Generally, each type of battery technology requires that the battery charge be maintained between minimum and maximum voltage levels, e.g. 3.0V and 4.2V in each cell. It should be appreciated that battery 32 may contain multiple cells, wired in series, and thus have any voltage from 1.0 V to 50V or even greater. Exceeding these limits may result in permanent damage and loss in performance and the extent of damage is a function of voltage and time. Once these limits have been exceeded, proper function of battery 32 cannot be guaranteed. The upper voltage limit in particular is very important in order to avoid damage to the battery, in the case of a lithium ion battery.

2. Improved battery longevity: the battery longevity can be preserved by knowing the aging state of the battery, i.e., when the battery is new, it is operated in more shallow cycles which is generally better for longevity. When the battery is older, the cycle life could be preserved, as any additional aging, due to deeper cycling, will be less significant.

3. Improved user knowledge: The techniques described herein can be used to indicate how long the electronic device can function without charging, thus enabling the user to make more informed choices about usage patterns, to increase battery life.

Minimize processing burden, despite varying current. The interrupt routine simply increments or decrements a charge counter every few seconds (or longer) and thus requires very little processing power. This is useful in a cochlear implant, for example, where the processor has a high utilization, and all instructions are optimized.

The characterizing method according to this invention is particularly suitable for low powered applications such as medical devices. In particular, it is envisaged that the techniques described herein can be advantageously used in devices where battery 32 is implanted in the human body. This situation brings in special challenges, as battery 32 is not easily replaceable and physical space must be minimized as far as possible. Accordingly, it is also desirable to keep the processing burden to a minimum.

An example of an implantable medical device which could benefit by using the techniques according to this disclosure is a totally implantable prosthetic hearing implant. Such an implant is described for example in WO 02/05590. The entire contents of this application is hereby incorporated by reference.

Figure 7:
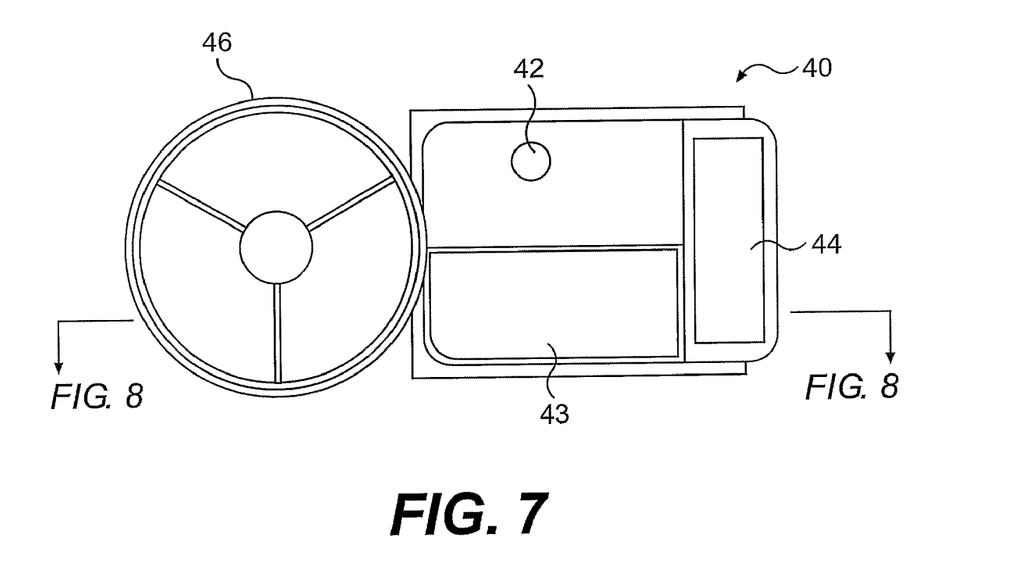
FIG. 7 is a plan view of a part of a totally implantable prosthetic hearing implant system in accordance with one embodiment of the present invention.
Figure 8:
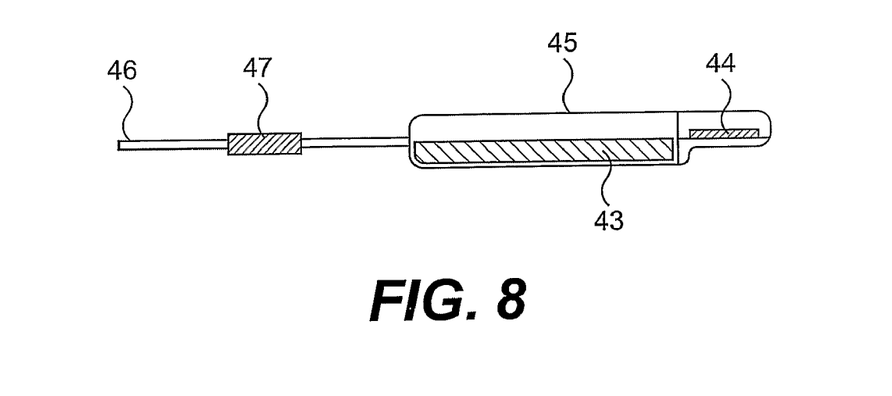
FIG. 8 is a cross-sectional view taken along the lines FIG. 8-FIG. 8 of FIG. 7.

Turning to FIGS. 7 and 8, one embodiment of the present invention is a cochlear implant 40 adapted for implantation in the temporal bone adjacent the ear comprises a coil 46, microphone 42, rechargeable battery 43 and speech/stimulation processor 44 incorporated within a single integrated device 40. As may be seen, the implant 40 also utilizes a coil 46 and a magnet 47. A housing 45 is provided to at least partially enclose rechargeable battery 43 and speech/stimulation processor 44.

Coil 46 also acts a power receiver and so provides a means of inductively charging battery 43 through the RF link. However, implant 40 is capable of operation while battery 43 is being recharged. Further, coil 46 acts as a RF link to allow bidirectional data transfer between implant 40 and external devices. For further methods of charging, the reader is referred to U.S. patent application Ser. No. 09/654,731, entitled "Transcutaneous Power Optimization Circuit for Cochlear Implant," filed Sep. 5, 2000.

Figure 9:
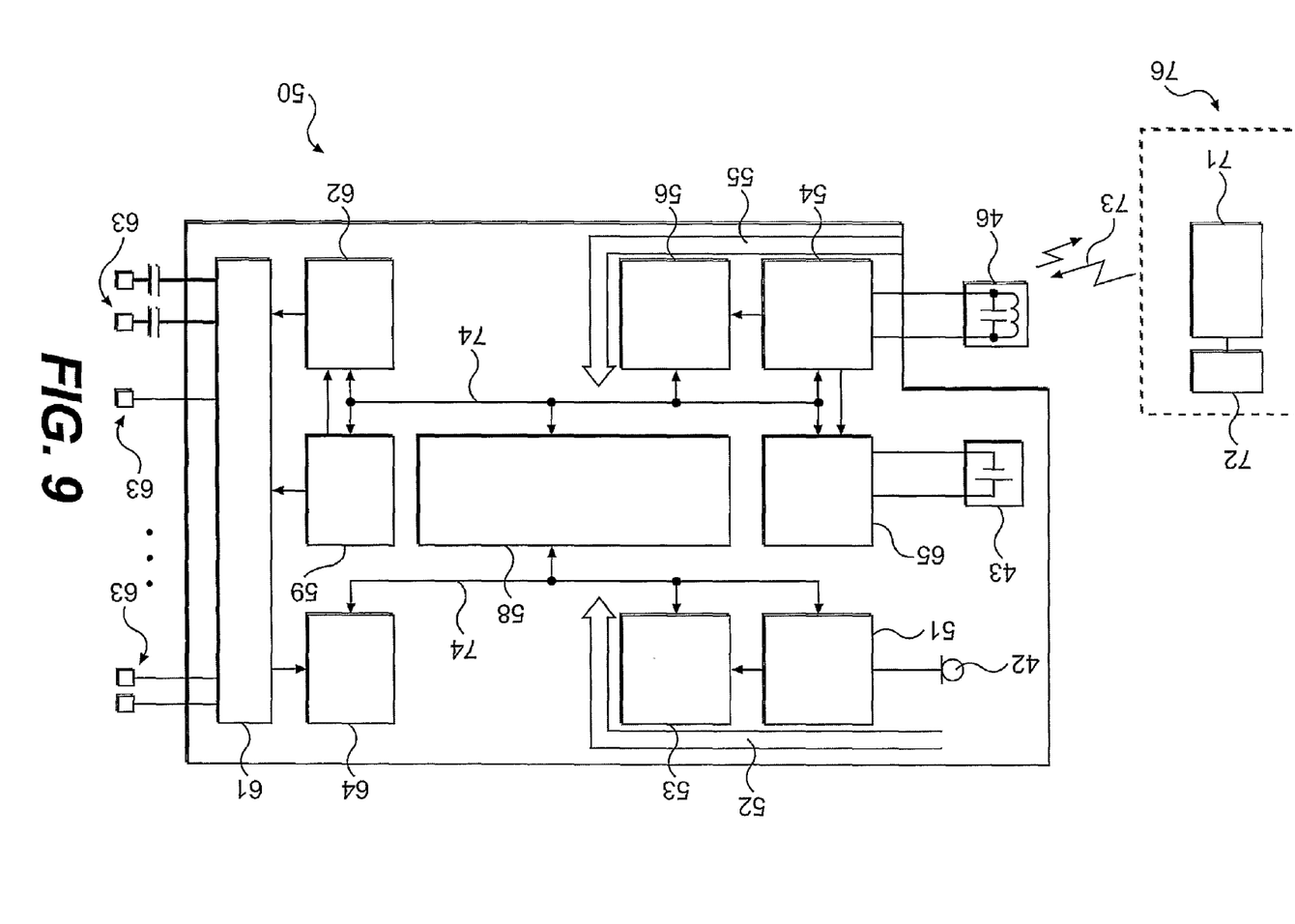
FIG. 9 is a schematic diagram of the electrical architecture used in the device of FIGS. 7 and 8 in accordance with one embodiment of the present invention.

Referring to FIG. 9, the electrical architecture 50 of the cochlear implant 40 is based on a microcontroller 58 which performs the main control functions. An internal audio signal path 52 includes internal microphone 42, front end 51 and sound processor 53. The external stimulus and control data path includes an RF Link (antenna coil) 46, RF controller 54, data encoder 56, output controller 59, current generator 62, electrode switch network and output stage 61, and cochlea electrodes 63.

An external controller 76 is also provided, having a battery charger 72 and auxiliary sound processor 71. Battery charger 72 provides a means of inductively recharging the implanted battery 43 through the RF link 73 when required. The external sound processor 71 can be used when the implanted processor is inactive for any reason and can provide wider sound coding algorithm options. The external controller can also provide a means of interrogating the implant 40 to determine the level of charge of the battery 43. Telemetry measurement circuit 64 performs measurements of electrode voltage.

A supply and bias block 65 provides power on reset to ensure all circuits start up in a controlled state at power up. Block 65 also provides charge management, to ensure that battery 43 charge cycles are properly maintained, supply voltage monitoring to ensure functional operation of and data retention, and voltage regulation. Block 65 also includes reference generators. Block 65 also ensures that low noise bias currents are distributed to the analog functions.

There can also be provided a deactivation means which provides a means of quickly and safely deactivating the implant 40, without the delay and inconvenience of having to locate and activate the external controller. On detection of operation of the deactivation means, microcontroller 58 places implant 40 in a standby mode where all electrical stimulation to the electrodes 63 is discontinued. If the implantee again operates the deactivation means, microcontroller 58 shuts down operation of implant 40. Implant 40 can then only be re-activated through use of external controller 76.

It should be appreciated that FIGS. 7, 8 and 9 illustrate a particular medical implant and that may be used with the teachings of the present invention. It should be appreciated that the charging technique described above may be utilized with this device or any other device and is not limited to the application of medical implants.

The techniques described herein may be implemented as software executing on a computer, such as microcontroller 58. Such software may be stored in a computer readable medium, including storage devices such as: a floppy disc, a hard disc drive, a magneto-optical disc drive, CD-ROM, magnetic tape or any other of a number of non-volatile storage devices well known to those skilled in the art.

The software is loaded into the computer from the computer readable medium, and then executed by the computer. A computer readable medium having such software or computer program recorded on it is a computer program product. The use of the computer program product in the computer preferably affects an advantageous apparatus for managing the charging and discharging of a rechargeable battery in accordance with the techniques described herein.

It will be appreciated by persons skilled in the art that numerous variations and/or modifications may be made to the invention as shown in the specific embodiments without departing from the spirit or scope of the invention as broadly described. The present embodiments are, therefore, to be considered in all respects as illustrative and not restrictive.

All documents, patents, journal articles and other materials cited in the present application are hereby incorporated by reference.

Although the present invention has been fully described in conjunction with several embodiments thereof with reference to the accompanying drawings, it is to be understood that various changes and modifications may be apparent to those skilled in the art. Such changes and modifications are to be understood as included within the scope of the present invention as defined by the appended claims, unless they depart therefrom.

What is claimed is:

1. A system for operating a rechargeable battery, said system comprising:
   means for charging said rechargeable battery to a predetermined maximum voltage;
   means for determining a first dynamic charging range for the rechargeable battery for a first plurality of charging cycles; and
   means for calculating an offset error for said determining means while there is no more than a relatively low load on the rechargeable battery,
   wherein the means for charging comprises:
      means for delivering a predetermined charging current to the battery until the battery is charged to the predetermined maximum voltage; and
      means for successively delivering progressively smaller charging currents to the battery until a predetermined minimum charging current of the progressively smaller charging currents is reached, wherein each of progressively smaller charging currents is delivered to the battery until the battery is charged to the predetermined maximum voltage.

2. The system according to claim 1, wherein the charging means is configured to deliver the decreasing charging currents after charging the rechargeable battery to said predetermined maximum voltage using the predetermined charging current.

3. The system according to claim 1, wherein said predetermined charging current and said predetermined minimum charging current are different.

4. The system according to claim 1, wherein said predetermined charging current may be dynamically adjusted based on parameters of said rechargeable battery.

5. The system according to claim 1, wherein said predetermined minimum charging current may be dynamically adjusted based on parameters of said rechargeable battery.

6. The system according to claim 1, wherein said predetermined maximum voltage may be dynamically adjusted based on parameters of said rechargeable battery.

7. The system according to claim 1, wherein said predetermined minimum charging current is less than 1 ampere.

8. The system according to claim 1, wherein said rechargeable battery is used for an implantable medical device.

9. The system according to claim 8, wherein said implantable medical device is a prosthetic hearing implant.

10. The system of claim 1, wherein the first dynamic charging range comprises first upper and lower charge values for the battery, wherein the first dynamic charge range is calculated based on a cumulative amount of charge delivered to the rechargeable battery during a first initial cycle,
   wherein the means for charging is configured to charge the rechargeable battery until the cumulative amount of charge equals the first upper charge value during each of the plurality of first charging cycles.

11. The system of claim 10, wherein the means for determining is configured to determine a second dynamic charging range for the rechargeable battery for a second plurality of charging cycles,
   wherein the second dynamic charging range comprises second upper and lower charge values for the rechargeable battery, wherein the second dynamic charge range is calculated based on a cumulative amount of charge delivered to the rechargeable battery during a second initial cycle after the plurality of first charging cycles, and
   wherein the means for charging is configured to charge the rechargeable battery until the cumulative amount of charge equals the second upper charge value during each of the plurality of second charging cycles.

12. The system according to claim 1, wherein the means for calculating the offset error calculates the offset error for said determining means while there is no load on the rechargeable battery.

13. A battery charger for a rechargeable battery of an electronic device, the battery charger comprising:
   a charge controller configured to charge the rechargeable battery during a cycle; and
   a measuring circuit configured to measure parametric data during the cycle, and to calculate an offset error of the measuring circuit while no load is placed on the rechargeable battery,
   wherein the measuring circuit comprises:
      a differential amplifier configured to amplify voltage drop across a sense resistor, and to output a current signal proportional to current flowing into or out of the rechargeable battery based thereon;
      an integrator configured to integrate the current signals from the differential amplifier;
      a detection block configured to output a voltage signal when the integration of the integrator reaches a threshold value; and
      digital logic configured to count the number of received output voltage signals.

14. The battery charger according to claim 13, wherein said measuring circuit is further configured to compensate for the calculated offset error of the measuring circuit.

15. The battery charger according to claim 13, wherein said parametric data includes a cumulative amount of charge delivered to the rechargeable battery during the first cycle.

16. The battery charger according to claim 13, wherein said electronic device is an implantable medical device.

17. The battery charger according claim 16, wherein the implantable medical device is a receiver/stimulator unit of prosthetic hearing implant system.

18. The battery charger of claim 13, further comprising:
   an auxiliary power source configured to power the electronic device independently of the rechargeable battery, and configured to power the measuring circuit independently of the rechargeable battery.

19. The battery charger according to claim 13, wherein the digital logic receives the detection signals from the detection block, maintain a count of the number of the detection signals received, and generate an asynchronous interrupt after receiving a predetermined number of the detection signals.

20. The battery charger of claim 19, wherein the measuring circuit further comprises:
a microcontroller configured to receive the asynchronous interrupt, calculate the offset error, and compensate for the offset error.

21. The battery charger of claim 19, wherein the measuring circuit is configured to periodically adjust the count maintained by the digital logic circuit so as to compensate for the calculated offset error of the measuring circuit.

22. The battery charger of claim 19, wherein the measuring circuit is configured to provide a clock signal to the digital logic circuit, wherein the digital logic circuit adjusts the count in accordance with a frequency of the clock signal so as to compensate for the calculated offset error of the measuring circuit, and wherein the frequency of the clock signal is the same as a frequency at which the detection block outputs the detection signals while no load is placed on the rechargeable battery.

23. The battery charger according to claim 13, wherein the measuring circuit is configured to calculate the offset error by calculating an offset current value of the measuring circuit, and is configured to compensate for the calculated offset error of the measuring circuit by providing to the integrator a compensating current value, wherein the offset current value and the compensating current value have the same magnitude and opposite signs.

24. The battery charger of claim 13, wherein the detection block is configured to receive an output voltage from the integrator, and wherein the output voltage signal outputted by the detection block is an output detection signal each indicating that a quantized unit of charge has been processed.

25. A battery charger for a rechargeable battery of an electronic device, the battery charger comprising:
a charge controller configured to charge the rechargeable battery during a first cycle;
a measuring circuit configured to measure one or more parametric data during the first cycle, and to calculate an offset error of the measuring circuit while no more than a relatively low load is placed on the rechargeable battery,
wherein the measuring circuit comprises:
a differential amplifier configured to amplify voltage drop across a sense resistor, and to output a current signal proportional to current flowing into or out of the rechargeable battery based thereon;
an integrator configured to integrate the current signals from the differential amplifier;
a detection block configured to receive an output voltage from the integrator, and configured to output detection signals each indicating that a quantized unit of charge has been processed; and
digital logic configured to count the number of received output detection signals.

26. The battery charger of claim 25, further comprising:
an auxiliary power source configured to power the electronic device independently of the rechargeable battery, and configured to power the measuring circuit independently of the rechargeable battery.

27. The battery charger according to claim 25, wherein the digital logic receives the detection signals from the detection block, maintain a count of the number of the detection signals received, and generate an asynchronous interrupt after receiving a predetermined number of the detection signals.

28. The battery charger of claim 27, wherein the measuring circuit further comprises:
a microcontroller configured to receive the asynchronous interrupt, calculate the offset error, and compensate for the offset error.

29. The battery charger according to claim 25, wherein said measuring circuit is further configured to compensate for the calculated offset error of the measuring circuit.

30. The battery charger according claim 29, wherein the implantable medical device is a receiver/stimulator unit of prosthetic hearing implant system.

31. The battery charger according to claim 25, wherein said electronic device is an implantable medical device.

32. The battery charger according to claim 25, wherein said parametric data includes a cumulative amount of charge delivered to the rechargeable battery during the first cycle.

* * * * *